United States Patent [19]
Kilbourn et al.

[11] 4,310,537
[45] Jan. 12, 1982

[54] ACETYL- AND CARBALKOXYTHIOUREIDOBENZOPHE-NONES

[75] Inventors: Edward E. Kilbourn, Chalfont; W. David Weir, Levitown, both of Pa.

[73] Assignee: Rohm and Haas Company, Philadelphia, Pa.

[21] Appl. No.: 840,452

[22] Filed: Oct. 7, 1977

Related U.S. Application Data

[62] Division of Ser. No. 694,746, Jun. 10, 1976, Pat. No. 4,060,636.

[51] Int. Cl.$^3$ ............... A01N 47/10; A01N 47/28; A61K 31/17; A61K 31/27
[52] U.S. Cl. ............... 424/300; 424/275; 424/309; 424/321; 424/322
[58] Field of Search ............... 424/300, 275, 309, 321

[56] References Cited

U.S. PATENT DOCUMENTS

| | | | |
|---|---|---|---|
| 3,796,710 | 3/1974 | Barker et al. | 260/243 R |
| 3,958,008 | 5/1976 | Hashimoto et al. | 424/300 |
| 4,005,217 | 1/1977 | Berg et al. | 424/300 |
| 4,048,326 | 9/1977 | Berg et al. | 424/300 |

FOREIGN PATENT DOCUMENTS

| | | | |
|---|---|---|---|
| 2129960 | 12/1971 | Fed. Rep. of Germany | 424/322 |
| 1340428 | 12/1973 | United Kingdom . | |
| 1350277 | 4/1974 | United Kingdom . | |

*Primary Examiner*—Allen J. Robinson
*Attorney, Agent, or Firm*—Terence P. Strobaugh

[57] ABSTRACT

Acetyl- and carbalkoxythioureidobenzophenones having a substituted amine adjacent to the thioureido radical are disclosed as having anthelmintic and antifungal activity.

8 Claims, No Drawings

ACETYL- AND CARBALKOXYTHIOUREIDOBENZOPHENONES

This is a division of application Ser. No. 694,746 filed June 10, 1976 now U.S. Pat. No. 4,060,636.

This invention relates to compositions containing acetyl- and carbalkoxythioureidobenzophenones as the active ingredient and methods of treating animals infested with helminths and of combatting fungi. Particularly, it relates to compositions wherein the active ingredient is an acetyl- or carbalkoxy thioureidobenzophenone.

Pharmacological studies emloying mice and sheep as the experimental animals indicate that the instant products and the compositions containing the active products are effective antifungal agents or anthelmintics which can be used in the treatment of conditions associated with helminths. The compounds are useful against pinworms (*Syphacia obvelata* and *Aspiculuris tetraptera*), dwarf tapeworm (*Hymenolepis nana*), trichostongyloid (*Nematospiroides dubius*), ascarid (*Ascaris suum*), liverfluke (*Fasciola hepatica*) and the like.

In accordance with the present invention, there are employed in the compositions for treating animals infested with helminths or of combatting fungi an active ingredient having the formula:

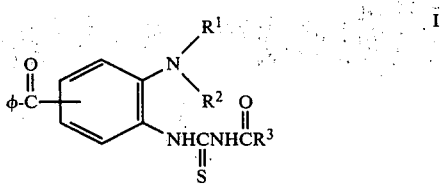

wherein $R^1$ is hydrogen, lower alkyl of from 1 to 5 carbon atoms such as methyl, ethyl, n-propyl, isopropyl, butyl, isobutyl, tert-butyl, pentyl and the like or mononuclear aralkyl such as benzyl and the like; $R^2$ is hydrogen, mononuclear aralkyl such as benzyl and the like or a radical of the formula:

wherein X is O or S and $R^4$ is lower alkyl of from 1 to 5 carbon atoms such as methyl, ethyl, propyl, n-butyl, pentyl and the like; halo substituted lower alkyl such as 1- or 2-chloroethyl; chloropropyl; 1- or 2-bromoethyl and the like; trifluoromethyl; lower alkenyl such as 1- or 2-propenyl, butenyl, pentenyl and the like; lower alkanoyl lower alkyl such as acetylmethyl, acetylpropyl, acetylbutyl, propionylmethyl, butyrylmethyl and the like; lower alkoxycarbonylalkyl such as methoxycarbonylmethyl, ethoxycarbonylmethyl, methoxycarbonylethyl, ethoxycarbonylethyl; mononuclear aryl such as phenyl and the like; substituted mononuclear aryl such as 4-nitrophenyl and the like; mononuclear aralkyl such as benzyl and the like; mononuclear arylamino such as phenylamino and the like; halo lower alkanoylamino such as chloroacetylamino, chloropropionylamino and the like; lower alkoxycarbonylamino such as methoxycarbonylamino and the like; substituted mononuclear arylsulfonylamino such as 4-methylphenylsulfonylamino and the like or $R^1$ and $R^2$, taken together with the nitrogen to which they are attached form a substituted imino radical, for example, iminothienyl lower alkyl such as iminothienylmethyl and the like or substituted imino mononuclear aryl lower alkyl such as imino-3-chloro-6-nitrophenylmethyl and the like; $R^3$ is methyl or lower alkoxy such as methoxy, ethoxy, propoxy, butoxy, pentoxy and the like with the proviso that when $R^1$ is hydrogen and $R^2$ is hydrogen, lower alkyl or

wherein $R^{4'}$ is lower alkyl or lower alkoxycarbonylamino, $R^3$ is methyl. Also, where appropriate, are also included the nontoxic, pharmaceutically acceptable salts thereof, for example, salts derived from the alkali metal and alkaline earth metal carbonates; hydroxide and lower alkoxides such as sodium carbonate, sodium hydroxide, magnesium carbonate, calcium hydroxide, potassium hydroxide, sodium methoxide and the like or from organic bases, for example, amines such as monoalkyl amines, dialkyl amines or heterocyclic amines such as methylamine, dimethylamine, triethylamine, piperidine, pyrrolidine, morpholine and the like. Also, where appropriate, acid addition salts such as the hydrochloride salts and the like.

A preferred embodiment of this invention are those compositions having as their active ingredient an effective amount of an acetyl- or carbalkoxythioureidobenzophenone selected from the following formulas:

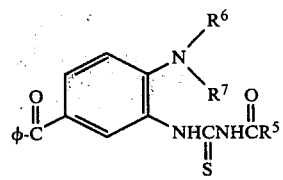

or

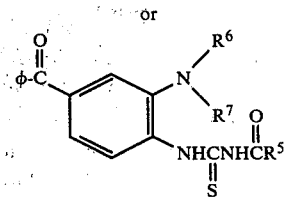

wherein $R^5$ is methyl or methoxy; $R^6$ is hydrogen or mononuclear aralkyl and $R^7$ is hydrogen, mononuclear aralkyl or a radical of the formula:

wherein X is O or S and $R^4$ is lower alkyl, halo substituted lower alkyl, trifluoromethyl, lower alkenyl, lower alkanoyl lower alkyl, lower alkoxycarbonylalkyl, mononuclear aryl, substituted mononuclear aryl, mononuclear aralkyl; mononuclear arylamino, lower alkoxycarbonylamino, substituted mononuclear arylsulfonylamino and the like with the proviso that when $R^6$ is hydrogen and $R^7$ is hydrogen or

wherein R4' is as defined above, R5 is methyl. The foregoing class of compounds exhibits particularly good anthelmintic activity and represents a preferred subgroup of compounds within the scope of this invention.

The thioureidobenzophenones (I, supra) of this invention are prepared by either of four alternative methods. One method comprises treating a thioureidoaminobenzophenone compound with a compound of the formula: (R2')2O or R2'Z wherein R2' and Z are as defined below. A second method comprises treating a mono- or diaminobenzophenone with an aldehyde. A third method comprises treating an R2" substituted aminobenzophenone with either a carbalkoxy isothiocyanate or acetyl isothiocyanate. A fourth method comprises treating an acetyl- or carbalkoxythioureidoaminobenzophenone with an isocyanate or isothiocyanate.

The following equation illustrates the first process:

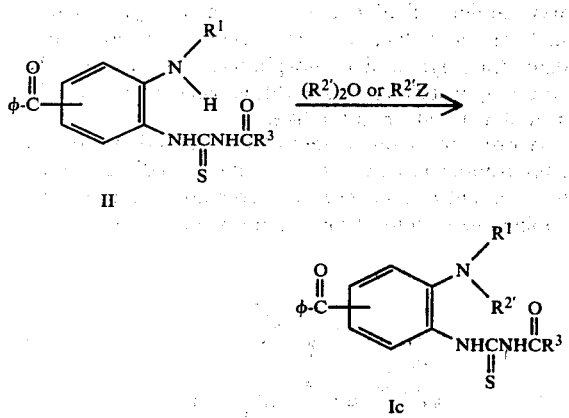

wherein R1, R3 and X are as defined above, R2' has the same definition as R2 excluding hydrogen and mononuclear aralkyl and Z is halo such as chloro and the like, lower alkanoyloxy such as acetoxy and the like or R2'Z is diketene. The reaction may be conducted at a temperature in the range of from 25° to 140° C. for a period of time in the range of from about five minutes to about 24 hours; however, the reaction is generally conducted at a temperature in the range of from about 60° to 132° C. for a period of time from about two hours to about 24 hours. Solvents which may be employed include benzene, ethyl acetate, toluene, chlorobenzene and the like.

The second method, which is employed to prepare those compounds wherein R1 and R2 taken together with the nitrogen to which they are attached forms a substituted imino radical, comprises treating a mono- or diaminobenzophenone with an aldehyde. The reaction is conducted at a temperature in the range of from about room temperature to the reflux temperature of the particular solvent employed. Solvents which may be employed include methanol, benzene, chlorobenzene and the like.

The third method is illustrated by the following equation:

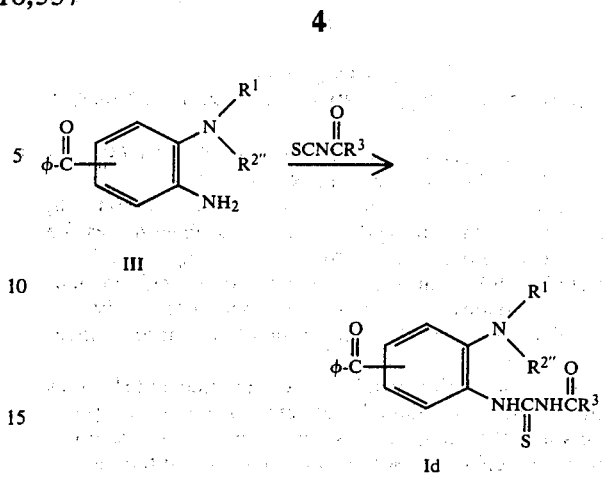

wherein R1 and R3 are as defined above and R2" has the same definition as R2 excluding hydrogen. The reaction may be conducted at a temperature in the range of from about 25° to about 60° C. for a period of time in the range of from about five minutes to about four days; however, the reaction is generally conducted at room temperature for a period of time from about one hour to about 18 hours. Solvents which may be employed include 1,2-dimethoxyethane, acetone, acetonitrile and the like.

A fourth method for preparing the acetyl- and carbalkoxythioureidobenzophenones wherein R2 is

comprises treating an acetyl- or carbalkoxythioureidoaminobenzophenone with an isocyanate or isothiocyanate under substantially the same reaction conditions as described in the third method. The following equation illustrates this process:

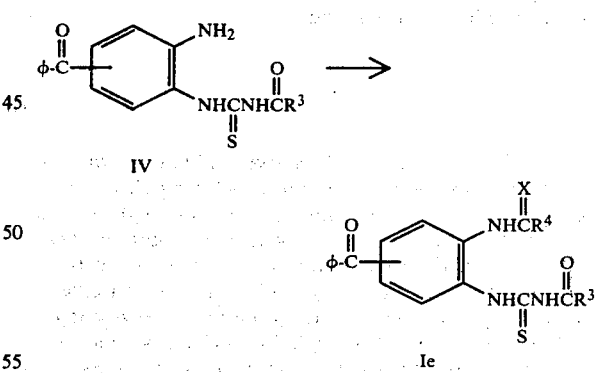

wherein R3, R4 and X are as defined above.

The aniline derivatives employed are known compounds disclosed in British Pat. No. 1,340,428.

All of the compounds described in this application can be employed as anthelmintics for combatting infections, for example, infections in avians, cats, dogs, sheep, porcine, bovine or equine. These compounds can be administered in liquid or tablet form to the host.

It is also within the scope of this invention to combine two or more compounds of this invention or to combine one or more of the compounds of this invention with known anthelmintics, such as thiabendazole, phenothiazine, piperazine, tetramisole, pyrantel, niclosamide or bunamidine.

Thus anthelmintic compositions of the invention comprise one or more of the anthelmintic compounds of the invention in a solid composition with a pharmaceutically acceptable diluent, coating agent, carrier, binder, filler, suspending agent, disintegrating agent, lubricant, feedstuff, diet supplement, thickening agent, preservative flavor and optionally another pharmaceutically active compound or in the form of a solution or dispersion of such a solid composition in a liquid diluent.

Solid compositions may suitably be provided in the form of a capsule, bolus, tablet or drench which are suitably prepared by intimately and uniformly mixing the active ingredient with suitable finely divided diluents, fillers, coating agents, disintegrating agents, lubricating agents, binders, thickening agents, and/or preservatives. Suitable binders include lactose, sodium chloride, kaolin, calcium sulfate, starch paste, calcium carbonate, gelatin, methyl cellulose and ethyl cellulose. Potato starch and dried corn are suitable disintegrators. Lubricants include calcium stearate, magnesium stearate, talc, hydrogenated vegetable oils and cocoa butter. Coating agents include acacia, kaolin, shellac, sucrose, powdered starch, cellulose acetate, phthalate, beeswax, polyvinylpyrrolidone and calcium carbonate. Examples of other carriers or diluents are solid orally ingestible carriers such as distillers dried grains, corn meal, citrus meal, fermentation residues, ground oyster shells, attapulgus clay, wheat shorts, molasses solubles, corn cob meal, edible vegetable substances, toasted dehulled soya flour, soybean mill feed, antibiotic mycellia, soya grits and crushed limestone. Further carriers or diluents include alcohol, glycerin and citric acid, thickening agents including tragacanth, carrageenin and pectin; surface active agents include sodium lauryl sulfate and benzalkonium chloride; preservatives include benzoic and sorbic acid.

Mixing of the anthelmintic agent with the other solid ingredients may be effected by grinding, stirring, milling or tumbling them together.

For capsules, the active ingredient is usually mixed with the other component(s) such as the diluent and then the mixture is charged into the capsule. Boluses usually contain the active ingredient, a binder and a lubricant compounded together.

A typical tablet formulation would include a binder, disintegrator, lubricant and coating.

The ingredients for capsules are generally agitated sufficiently to obtain a uniformly powdered product which is then utilized for the filling of gelatin capsules, both the hard-shelled and soft elastic types. Capsules should be chosen which are of such a size as to be capable of accomodating a sufficient quantity of material to provide an effective amount of anthelmintic per unit. Of course, larger or smaller capsules for different concentrations of active agent may be readily employed where desired or necessitated.

Where an animal is afflicted with helminthiasis, the treatment thereof comprises the oral administration in a therapeutically effective amount of at least one of the anthelmintics of the invention. The actual dosage to be administered at one time or over any extended period will, of course, vary with the particular animal being treated.

The active ingredient may be administered in the form of a liquid drench or in emulsion. In the former application the solid active ingredient is usually mixed with a suspending agent such as bentonite and the solid product is added to water just before administration.

The active ingredient may be administered in animal feed formulations. The active ingredient compounded with a carrier and/or any other ingredient mentioned above may be in pellet form for admixture, for example, with pellet form sheep feed. Furthermore, when the diluent is sodium chloride, the anthelmintic agent can be administered in the form of a salt lick or salt block.

For use against helminths, the prepared compounds are most desirably administered between about 10 and 150 mg./kg. of body weight.

In addition to their use as anthelmintic agents, the compounds of Formula I have also been found to display antifungal activity. It is contemplated that antifungal compositions containing these compounds as an essential active ingredient can be employed in controlling the growth of fungi in or on animals and plants as well as in paint, wood, textile, cosmetic, leather, tobacco, fur, rope, paper, pulp, plastic, fuel, rubber and food industries. The compounds of Formula I may be incorporated into diverse formulations such as solids, including finely divided powders and granular materials, as well as liquids, such as solutions, emulsions, suspensions, concentrates, emulsifiable concentrates, slurries and the like, depending upon the application intended and the formulation media desired. Thus it will be appreciated that the compounds of this invention may be employed to form fungicidally active compositions containing a fungicidally active quantity of such compounds as an essential active ingredient. Such compositions may also contain finely divided dry or liquid diluents, extenders, fillers, conditioners and excipients including various clays, diatomaceous earth, talc, and the like, or water and various organic liquids, for example, lower alkanols such as ethanol and isopropanol, or kerosene, benzene, toluene and other petroleum distillate fractions or mixtures thereof. The formulations contain from about 50 to 800 parts per million of active ingredient and preferably from about 200 to 500 parts per million.

Preferred embodiments of compositions of the invention are now given in the following examples showing formulations for tablets and chewable tablets.

EXAMPLE I

A tablet of the following composition is formulated:

| | |
|---|---|
| Active Compound | 220 mg. |
| Lactose | 53.23 mg. |
| Magnesium Aluminum Silicate Gel | 2.24 mg. |
| Starch | 13.13 mg. |
| Calcium Stearate | 0.65 mg. |
| Microcrystalline Cellulose | 35.75 mg. |
| TOTAL | 325 mg. |

A granulation, containing water by the use of magnesium aluminum silicate and starch in the form of pastes, is tableted to form flat level, double or quarter scored, uncoated tablets, of 6 to 9 S.C.A. hardness. The appropriate number (and fraction) of tablets is administered to the host, e.g., one tablet per 20 lbs. body weight.

EXAMPLE II

An alternate formulation is in the form of a palatable chewable tablet. Each chewable tablet contains:

| | |
|---|---|
| Active Compound | 110 mg. |
| Dried Fish Meal | 1027 mg. |
| Dried Liver Powder, Bovine | 1027 mg. |
| Soybean Oil Meal | 97 mg. |
| Cane Sugar | 239 mg. |
| TOTAL | 2500 mg. |

Included within the scope of this invention are the nontoxic, pharmacologically acceptable salts of the instant products. In general, any base which will form a salt with the acetyl or carbalkoxythioureidobenzophenones and whose pharmacological properties will not cause an adverse physiological effect when ingested by the body system is considered as being within the scope of this invention. Suitable bases thus include, for example, those derived from the alkali metals and alkaline earth metals, for example, the alkali metal and alkaline earth metal carbonates, hydroxides and alkoxides such as sodium carbonate, sodium hydroxide, magnesium carbonate, calcium hydroxide, potassium hydroxide, sodium ethoxide and the like, ammonia, primary, secondary and tertiary amines, for example, mono-lower alkylamines such as methylamine, ethylamine and the like, di-lower alkylamines such as dimethylamine, diethylamine and the like, tri-lower alkylamines such as triethylamine and the like, alicyclic amines such as cyclopentylamine and the like, or heterocyclic amines such as piperidine, pyrrolidine, morpholine and the like.

The examples which follow illustrate the acetyl and carbalkoxythioureidobenzophenones of this invention and the method by which they are prepared. However, the examples are illustrative only and it will be apparent to those having ordinary skill in the art that all of the products embraced by Formula I and Ic (supra) may also be prepared in an analogous manner by substituting the appropriate starting materials for those set forth in the examples.

When compounds of Formula I (supra) can exist in various isomer and stereoisomer forms all such isomers and their mixtures and racemates are included within the scope of this invention.

EXAMPLE 1

3-(3-Carbomethoxythioureido)-4-acetylacetamidobenzophenone

To a suspension of 3-(3-carbomethoxythioureido)-4-aminobenzophenone (3.29 g.) in toluene (200 ml.) is added a 50% solution of diketene (1.68 g.) in acetone. The mixture is refluxed, with stirring, for 18 hours. The hot toluene solution is decanted from the oily residue in the reaction flask to afford 1.35 g. of crude product. To the toluene filtrate is added hexane (500 ml.) which affords, upon filtration, an additional 1.25 g. of 3-(3-carbomethoxythioureido)-4-acetylacetamidobenzophenone.

EXAMPLE 2

3-(3-Carbomethoxythioureido)-4-chloroacetamidobenzophenone

To a suspension of 3-(3-carbomethoxythioureido)-4-aminobenzophenone (3.29 g.) in toluene (200 ml.) is added chloroacetyl chloride (1.13 g.; 0.01 mole). The reaction mixture is refluxed with stirring for two hours and the cloudy solution formed is allowed to stand overnight at room temperature. The solid is collected by filtration and washed with hexane and dried to afford 3.3 g. (81% yield) of 3-(3-carbomethoxythioureido)-4-chloroacetylamidobenzophenone.

EXAMPLE 3

3-(3-Carbomethoxythioureido)-4-carboethoxyacetamidobenzophenone

To a suspension of 3-(3-carbomethoxythioureido)-4-aminobenzophenone (3.29 g.; 0.01 mole) in toluene (200 ml.) is added ethylmalonyl chloride (1.51 g.; 0.01 mole). The mixture is refluxed for 18 hours. Upon cooling, a tan precipitate forms. Hexane (600 ml.) is added and a precipitate is collected by filtration, washed with hexane and then dried to afford 1.6 g. (36% yield) of 3-(3-carbomethoxythioureido)-4-carboethoxyacetamidobenzophenone. m.p. 60°–70° C., dec.

EXAMPLE 4

3-(3-Carbomethoxythioureido)-4-(3-acetylthioureido)benzophenone

To a suspension of 3-(3-carbomethoxythioureido)-4-aminobenzophenone (1.2 g.; 0.0036 mole) in acetone (15 ml.) is added acetyl isothiocyanate (0.37 g.; 0.0036 mole). The reaction mixture is heated to reflux and then allowed to stand at room temperature for 18 hours. The product is collected by filtration, washed successively to afford 0.85 g. (54% yield) of 3-(3-carbomethoxythioureido)-4-(3-acetylthioureido)benzophenone, m.p. 210° C., dec.

Elemental Analysis for $C_{19}H_{18}N_4O_4S_2$: Calc.: C, 53.01; H, 4.21; N, 13.02, Found: C, 53.64; H, 4.26; N, 12.53.

EXAMPLE 5

3-(3-Acetylthioureido)-4-Aminobenzophenone

To a stirred solution of 3,4-diaminobenzophenone (8.48 g.; 0.04 mole) in ethyl ether (1.0 L.) there is added dropwise acetyl isothiocyanate (4.04 g.; 0.04 mole). The solution is stirred at room temperature for two hours and a precipitate collected by filtration and dried to afford 10.7 g. (85% yield) of 3-(3-acetylthioureido)-4-aminobenzophenone, m.p. 211° C., dec.

Elemental Analysis for $C_{16}H_{15}N_3O_2S$: Calc.: C, 61.32; H, 4.83; N, 13.41, Found: C, 61.00; H, 4.81; N, 13.04.

EXAMPLE 6

3-(3-Carbomethoxythioureido)-4-(3-p-toluenesulfonylureido)benzophenone

To a suspension of 3-(3-carbomethoxythioureido)-4-aminobenzophenone (1.0 g.; 0.00304 mole) in acetone (5 ml.) is added p-toluenesulfonyl isocyanate (0.6 g.; 0.00304 mole). The suspension is heated to 50° C. and vacuum filtered. The precipitate is washed with acetone and ether and then dried to afford 0.4 g. (29% yield) of 3-(3-carbomethoxythioureido)-4-(3-p-toluenesulfonylureido)benzophenone, m.p. 191°–192° C., dec.

Elemental Analysis for $C_{24}H_{22}N_4O_6S_2$: Calc.: C, 54.74; H, 4.21; N, 10.64, Found: C, 54.21; H, 4.91; N, 10.65.

EXAMPLE 7

3-(Imino-2-thienylmethyl)-4-(3-carbomethoxythioureido)benzophenone

To a solution of 3-(imino-2-thienylmethyl)-4-aminobenzophenone (1.0 g.) in acetone (5 ml.) is added carbomethoxy isothiocyanate (0.38 g.). The solution is allowed to stand at room temperature for one hour and then the precipitate is collected by filtration, washed successively with acetone and ether and then dried to afford 0.55 g. of 3-(imino-2-thienylmethyl)-4-(3-carbomethoxythioureido)benzophenone, m.p. 194° C., dec.

EXAMPLE 8

3-(3-Carbomethoxythioureido)-4-(imino-2-thienylmethyl)benzophenone

A mixture of 3-(3-carbomethoxythioureido)-4-aminobenzophenone (3.29 g.), 2-thiophenecarboxaldehyde (1.12 g.) and p-toluenesulfonic acid monohydrate (0.2 g.) in toluene (150 ml.) is heated to reflux for five minutes and then allowed to stir at room temperature over the week-end. The reaction mixture is again refluxed for five hours. The reaction mixture is filtered hot and the precipitate which forms upon cooling is collected and dried to afford 2.6 g. (61.3% yield) of 3-(3-carbomethoxythioureido)-4-(imino-2-thienylmethyl)benzophenone, m.p. 159°–165° C., dec.

Elemental Analysis for $C_{21}H_{17}N_3O_3S_2$: Calc.: C, 59.55; H, 4.05; N, 9.92, Found: C, 59.77; H, 4.01; N, 10.25.

EXAMPLE 9

3-(3-Acetylthioureido)-4-(3-carbomethoxythioureido)benzophenone

To a suspension of 3-(3-acetylthioureido)-4-aminobenzophenone (1.1 g.) in acetone (15 ml.) is added carbomethoxy isothiocyanate (0.41 g.). The mixture is heated to reflux and then is stirred at room temperature for 18 hours. The crude product is collected by filtration, washed with acetone and ether and then dried to afford 0.6 g. (40% yield) of 3-(3-acetylthioureido)-4-(3-carbomethoxythioureido)benzophenone, m.p. 203°–204° C., dec.

Elemental Analysis for $C_{19}H_{18}N_4O_4S_2$: Calc.: C, 53.01; H, 4.21; N, 13.02, Found: C, 53.36; H, 4.28; N, 12.81.

EXAMPLE 10

3-(3-Acetylthioureido)-4-[3-(4'-fluoro-3'-nitrophenylureido)]benzophenone

To a suspension of 3-(3-acetylthioureido)-4-aminobenzophenone (1.565 g.) in acetone (25 ml.) is added 4-fluoro-3-nitrophenyl isocyanate (0.91 g.). The suspension is refluxed and then allowed to stir at room temperature for three hours. The thick suspension is filtered and washed with acetone and ether and then dried to afford 1.15 g. (46.4% yield) of 3-(3-acetylthioureido)-4-[3-(4'-fluoro-3'-nitrophenylureido)]benzophenone, m.p. 212°–214° C., dec.

EXAMPLE 11

3-(3-Carbomethoxythioureido)-4-benzylaminobenzophenone

To a solution of 3-amino-4-benzylaminobenzophenone (1.51 g.) in glyme (25 ml.) is added carbomethoxy isothiocyanate (0.59 g.). The solution is maintained at room temperature for four days and then poured into water. The precipitate which forms is collected, washed with water and dried to afford 1.8 g. of 3-(3-carbomethoxythioureido)-4-benzylaminobenzophenone as a yellow solid, m.p. 75°–79° C. with dec. at 105° C.

Elemental Analysis for $C_{23}H_{21}N_3O_2S$: Calc.: C, 65.85; H, 5.09; N, 10.02, Found: C, 65.25; H, 5.09; N, 9.89.

EXAMPLE 12

3-(3-Carbomethoxythioureido)-4-phenylacetamidobenzophenone

To a suspension of 3-(3-carbomethoxythioureido)-4-aminobenzophenone (3.29 g.) in toluene (100 ml.) is added phenylacetyl chloride (1.55 g.). The mixture is refluxed for two hours and allowed to stand at room temperature overnight. The precipitate is collected by filtration, washed with hexane and dried to afford 2.5 g. of 3-(3-carbomethoxythioureido)-4-phenylacetamidobenzophenone, m.p. 202°–204° C., dec.

Elemental Analysis for $C_{24}H_{21}N_3O_4S$: Calc.: C, 64.41; H, 4.73; N, 9.39, Found: C, 64.33; H, 4.72; N, 9.51.

EXAMPLE 13

3-(3-Carbomethoxythioureido)-4-trifluoroacetamidobenzophenone

To a suspension of 3-(3-carbomethoxythioureido)-4-aminobenzophenone (3.29 g.) in toluene (100 ml.) is added trifluoroacetic anhydride (2.1 g.). The solution is refluxed for two hours and allowed to stand at room temperature overnight. The precipitate is collected, washed with hexane and dried to afford 2.5 g. of 3-(3-carbomethoxythioureido)-4-trifluoroacetamidobenzophenone as a white solid, m.p. 183°–184° C., dec.

Elemental Analysis for $C_{18}H_{14}F_3B_3O_4S$: Calc.: C, 50.82; H, 3.32; N, 9.88, Found: C, 50.39; H, 3.08; N, 9.58.

EXAMPLE 14

3-(3-Carbomethoxythioureido)-4-p-nitrobenzamidobenzophenone

To a suspension of 3-(3-carbomethoxythioureido)-4-aminobenzophenone (3.29 g.) in toluene (200 ml.) is added p-nitrobenzyl chloride (1.86 g.). The mixture is refluxed for 18 hours and then cooled to room temperature. The precipitate is collected by filtration, washed with hexane and dried to afford 4.15 g. (87% yield) of 3-(3-carbomethoxythioureido)-4-p-nitrobenzamidobenzophenone, m.p. 205° C., dec. at 210° C.

Elemental Analysis for $C_{23}H_{18}N_4O_6S$: Calc.: C, 57.73; H, 3.79; N, 11.71, Found: C, 57.56; H, 3.9; N, 11.73.

EXAMPLE 15

3-(3-Carbomethoxythioureido)-4-benzamidobenzophenone

To a suspension of 3-(3-carbomethoxythioureido)-4-aminobenzophenone (3.29 g.) in toluene (200 ml.) is added benzoyl chloride (1.4 g.). The mixture is refluxed for 18 hours, cooled to room temperature and the precipitate collected, washed with hexane and dried to afford 2.8 g. (65% yield) of 3-(3-carbomethoxythioureido)-4-benzamidobenzophenone as a gray solid, m.p. 191°–192° C., dec.

Elemental Analysis for $C_{23}H_{19}N_3O_4S$: Calc.: C, 63.73; H, 4.42; N, 9.69, Found: C, 63.70; H, 4.50; N, 9.72.

EXAMPLE 16

3-(3-Carbomethoxythioureido)-4-(3-phenylureido)benzophenone

To a suspension of 3-(3-carbomethoxythioureido)-4-aminobenzophenone (3.0 g.) in acetone (100 ml.) is added phenyl isocyanate (1.08 g.). The reaction mixture is refluxed for 1½ hours and then allowed to stand at room temperature overnight. The precipitate is collected, washed with ether and dried to afford 2.65 g. (65% yield) of 3-(3-carbomethoxythioureido)-4-(3-phenylureido)benzophenone as a white solid, m.p. 212° C., dec.

Elemental Analysis for $C_{23}H_{20}N_4O_4S$: Calc.: C, 61.59; H, 4.50; N, 12.49, Found: C, 61.43; H, 4.50; N, 12.48.

By following substantially the procedure of Example 16 and by substituting the phenyl isocyanate described therein, equimolar quantities of 2-bromopropionyl chloride, 4-chlorobutyryl chloride, 3-carbomethoxypropionyl chloride, 3-chloropropionyl chloride, 2-chloropropionyl chloride, 2-nitro-5-chlorobenzaldehyde, chloroacetyl isocyanate, crotonyl chloride, 2-thiophenecarboxaldehyde and acetyl chloride, there is prepared:

| | |
|---|---|
| 3-(3-carbomethoxythioureido)-4-(2-bromopropionamido)benzophenone | m.p. 190° C., dec.; |
| 3-(3-carbomethoxythioureido)-4-(4-chlorobutyramido)benzophenone | m.p. 186° C., dec.; |
| 3-(3-carbomethoxythioureido)-4-(3-carbomethoxypropionamido)benzophenone | m.p.174°–176° C., dec.; |
| 3-(3-carbomethoxythioureido)-4-(3-chloropropionamido)benzophenone | m.p. 197°–199° C., dec.; |
| 3-(3-carbomethoxythioureido)-4-(2-chloropropionamido)benzophenone | m.p. 201°–203° C., dec.; |
| 3-(3-carbomethoxythioureido)-4-(imino-5-chloro-2-nitrophenylmethyl)benzophenone | m.p. 217° C., dec.; |
| 3-(3-carbomethoxythioureido)-4-(3-chloroacetylureido)benzophenone | m.p. 209° C., dec.; |
| 3-(3-carbomethoxythioureido)-4-crotonamidobenzophenone | m.p. 186° C.–188° C., dec.; |
| 3-(3-acetylthioureido)-4-(imino-2-thienylmethyl)benzophenone | m.p. 190° C., dec. and |
| 3-(3-acetylthioureido)-4-acetamidobenzophenone | m.p. 199°–201° C., dec. |

EXAMPLE 17
3-(3-Carbomethoxythioureido)-4-(N-benzyl-N-acetamido)benzophenone To a suspension of 3-(3-carbomethoxythioureido)-4-benzylaminobenzophenone (1.9 g.) in toluene (100 ml.) is added acetyl chloride (0.36 g.). The mixture is refluxed three hours and stirred at room temperature over the weekend. The precipitate is collected by filtration, washed with hexane and dried to afford 0.7 g. (34% yield) of 3-(3-carbomethoxythioureido)-4-(N-benzyl-N-acetamido)-benzophenone, m.p. 178° C., dec.

Elemental Analysis for $C_{19}H_{18}BrN_3O_4S$: Calc.: C, 49.14; H, 3.91; N, 9.05, Found: C, 49.14; H, 3.79; N, 8.95.

EXAMPLE 18
3-(3-Carbomethoxythioureido)-4-(N-n-butyl-N-acetamido)benzophenone Step A—3-(Nitro-n-butylamino)benzophenone A mixture of 4-chloro-3-nitrobenzophenone (13.08 g.; 0.05 mole) and n-butylamine (10.97 g.; 0.15 mole) are refluxed and stirred for four hours. To the reaction mixture is added water(300 ml.) and toluene (200 ml.) and the toluene layer collected and dried over magnesium sulfate. The toluene solution is filtered and the toluene removed under vacuum to afford 11.4 g. of 3-nitro-4-butylaminobenzophenone.

Step B—3-Amino-4-n-butylaminobenzophenone

To a solution of 3-(nitro-4-n-butylamino)-benzophenone (5.96 g.; 0.02 mole) in ethanol (200 ml.) is added palladium on charcoal (5%; 0.1 g.). The mixture is hydrogenated until theoretical uptake of hydrogen has occurred (about three hours) and then let stand at room temperature overnight. The reaction mixture is filtered to remove the catalyst and the filtrate concentrated under vacuum to afford 4.75 g. (88.6% yield) of 3-amino-4-n-butylaminobenzophenone.

Step C—3-(3-Carbomethoxythioureido)-4-n-butylaminobenzophenone

To a solution of 3-amino-4-n-butylaminobenzophenone (2.38 g.) in diethyl ether (200 ml.) is added carbomethoxy isothiocyanate (1.4 g.). The reaction mixture is stirred at room temperature for three hours. The product is collected by filtration and dried to afford 0.2 g. of product, m.p. 160°–162° C., dec. The filtrate is allowed to stand overnight at room temperature and a second crop is collected amounting to 0.15 g., m.p. 162° C., dec. The total amount of 3-(3-carbomethoxythioureido)-4-n-butylaminobenzophenone obtained is 0.35 g. (10.2% yield).

Step D—3-(3-Carbomethoxythioureido)-4-N-n-butyl-N-acetamido)benzophenone

To a mixture of 3-(3-carbomethoxythioureido)-4-n-butylaminobenzophenone (3.85 g.; 0.01 mole) in toluene (200 ml.) is added acetyl chloride (0.785 g.; 0.01 mole). The mixture is refluxed for three hours and is stirred at room temperature for 18 hours. The mixture is vacuum filtered to afford 3-(3-carbomethoxythioureido)-4-(N-n-butyl-N-acetamido)benzophenone.

What is claimed is:

1. A composition useful as an anthelmintic or antifungal agent which comprises an effective amount of 3-(3-carbomethoxythioureido)-4-(3-acetylthioureido)benzophenone.

2. A composition useful as an anthelmintic or antifungal agent which comprises an effective amount of 3-(3-acetylthioureido)-4-(3-carbomethoxythioureido) benzophenone.

3. A composition useful as an anthelmintic or antifungal agent which comprises an effective amount of 3-(carbomethoxythioureido)-4-benzylaminobenzophenone.

4. A composition useful as an anthelmintic or antifungal agent which comprises an effective amount of 3-(3-carbomethoxythioureido)-4-crotonamidobenzophenone.

5. A method for treating animals infested with helminths which comprises the administration to an animal in need of such treatment an effective amount of 3-(3-carbomethoxythioureido)-4-(3-acetylthioureido)benzophenone.

6. A method for treating animals infested with helminths which comprises the administration to an animal in need of such treatment an effective amount of 3-(3-acetylthioureido)-4-(3-carbomethoxythioureido)benzophenone.

7. A method for treating animals infested with helminths which comprises the administration to an animal in need of such treatment an effective amount of 3-(3-carbomethoxythioureido)-4-benzylaminobenzophenone.

8. A method for treating animals infested with helminths which comprises the administration to an animal in need of such treatment an effective amount of 3-(3-carbomethoxythioureido)-4-crotonamidobenzophenone.

* * * * *